United States Patent [19]
Hayakawa et al.

[11] Patent Number: 5,804,050
[45] Date of Patent: Sep. 8, 1998

[54] OXYGEN SENSOR WITH A HEATER

[75] Inventors: Nobuhiro Hayakawa; Syogo Kawajiri; Yoshiro Noda; Hiroshi Miyata; Satoshi Ishikawa; Shoji Akatsuka, all of Nagoya, Japan

[73] Assignee: NGK Spark Plug Co., Ltd., Nagoya, Japan

[21] Appl. No.: 869,414

[22] Filed: Jun. 4, 1997

[30] Foreign Application Priority Data

Jun. 5, 1996 [JP] Japan ................................ 8-166717
Apr. 28, 1997 [JP] Japan ................................ 9-124987

[51] Int. Cl.⁶ .............................. G01N 27/26; G01N 7/00
[52] U.S. Cl. ...................... 204/424; 204/408; 204/428; 205/785; 73/23.32
[58] Field of Search ................ 73/31.05, 23.2, 73/23.31, 23.32; 204/421, 424, 428, 429, 426, 425, 427, 408, 422, 423; 205/785, 784, 783.5

Primary Examiner—Hezron E. Williams
Assistant Examiner—Jay L. Politzer
Attorney, Agent, or Firm—Morgan, Lewis & Bockius LLP

[57] ABSTRACT

A shaft-like heating member is inserted into and fixed to an oxygen sensing element of a hollowed shaft-like member, together with of a terminal member. A heating portion is located at a portion of the heating member closer to the extreme end thereof. The surface of the heating portion is resiliently pressed on the element inner wall in a side-abutting fashion. In this case, a guide mainly gives rise to the elastic force. With such a side-abutting structure, heat generated in the heating portion is directly transferred to the oxygen sensing element, and heats it. Heat radiated from a portion in the vicinity of its contact position additively heats the oxygen sensing element. Temperature of the oxygen sensor quickly reaches an activation temperature.

24 Claims, 12 Drawing Sheets

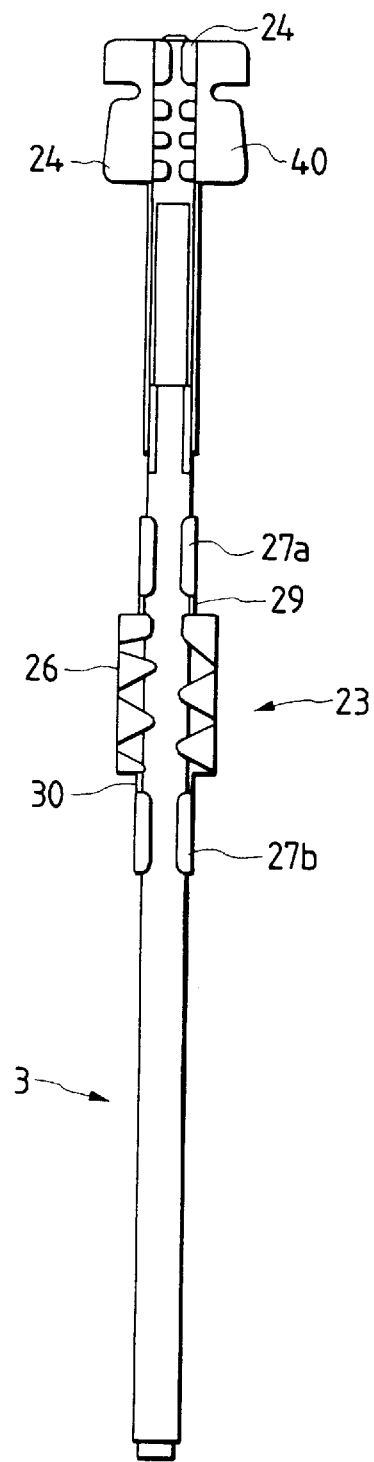
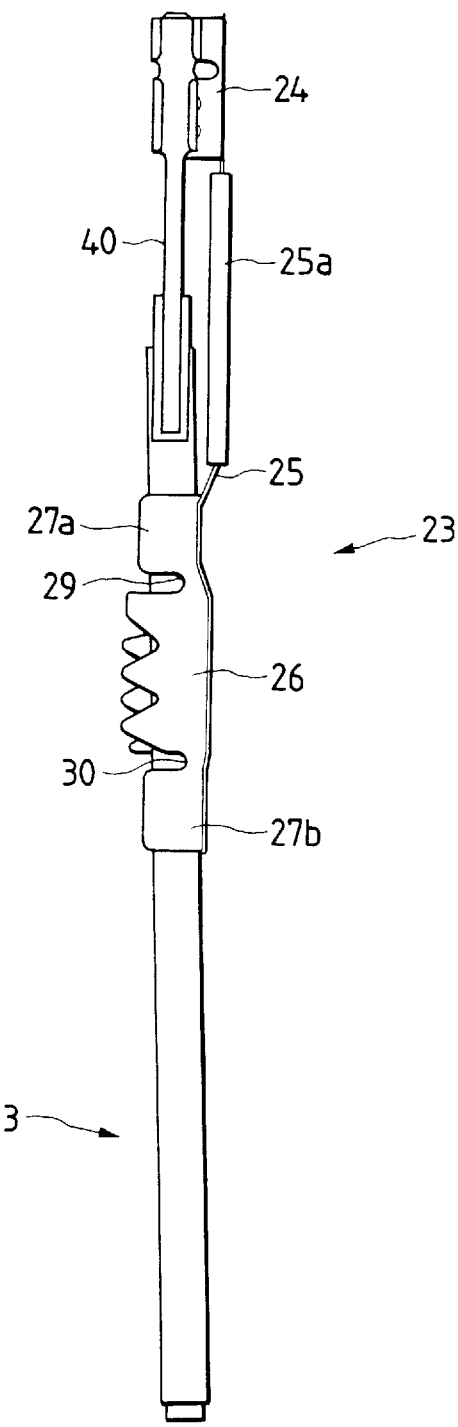

$\tan \theta = \dfrac{d}{L}$ $d = L \tan \theta$ $0.1° \leqq \theta \leqq 0.5°$ $0.0017L \leqq d \leqq 0.0087L$

OXYGEN SENSOR WITH A HEATER

BACKGROUND OF THE INVENTION

1. Field of the Invention

The present invention relates to an oxygen sensor for sensing an oxygen concentration in exhaust gases of an internal combustion engine or an oxygen sensor for sensing oxygen in a specific gas. More particularly, the present invention relates to an oxygen sensor with a heater which can quickly heat the oxygen sensor up to its activation temperature.

2. Description of the Related Art

Recently, there is an increasing demand of the purifying of exhaust gases from an internal combustion engine of an automobile, for example. In this circumstance, an oxygen sensor with a heater is developed which is able to well sense an oxygen concentration in the exhaust gases from the internal combustion engine even under a condition that the exhaust gas temperature is low, for example, at the engine start or the time of idling. Unexamined Japanese Patent Publication (kokai) No. Hei. 4-157358, for example, discloses an oxygen sensor which includes an oxygen sensing element of a hollowed shaft-like member having a closed end and an electrode layer on the inner wall thereof, and a shaft-like heating member, which is disposed within the oxygen sensing element, for heating the oxygen sensing element. In the oxygen sensor, a shaft (bar)=like heating member (heater) is coaxially inserted into the inner space of the test-tube like oxygen sensing element, which is made of solid electrolyte of an oxygen iron conduction till the extreme end of it reaches or is in proximity to the inner surface of the extreme end of the sensing element.

In this type of the oxygen sensor, when the oxygen sensing element is heated not uniformly, sufficiently heated and activated portions and insufficiently heated and high resistance portions coexist in the oxygen sensing element. An electrically resistance of the whole sensing element is frequently determined by the high resistance portions. The result will be an elongation of a time lasting till the element resistance value is satisfactorily low and the element is activated, viz., a rise time of the sensor. In the conventional sensor construction, the heating member is disposed coaxially with the oxygen sensing element, the oxygen sensing element is uniformly heated in the circumferential direction, and therefore is uniformly activated in the same direction. The extreme end of the heating member is in contact with or in proximity to the inner surface of the extreme end of the oxygen sensing element. Therefore, a heat transfer from the extreme end of the heating member to the oxygen sensing element will be in a satisfactory level. In this respect, the end to reduce the rise time of the sensor will be achieved to some extent.

However, the conventional sensor has the following problems to be solved. When the bar-like heating member and/or the hollowed oxygen sensing element is thermally expanded, the extreme end of the heating member is spaced apart from the inner surface of the extreme end of the oxygen sensing element, so that a heat transfer efficiency is deteriorated. At the time of thermally expanding the member and the element, it may happen that the extreme end of the heating member is pressed against the inner surface of the extreme end of the oxygen sensing element. In this case, a stress is forcibly generated, which adversely affects the device durability. Thus, the oxygen sensor is greatly influenced by the thermal expansion. This leads to a nonuniformity of the heating state of the oxygen sensing element and a variation of the characteristics of the oxygen sensors. A possible approach to solve this problem is that a relatively large space is formed between the heating member and the oxygen sensing element. However, the approach fails in solving the problem because the heat transfer efficiency is lowered, and the sensor rise time is long.

For example, the heating member contacts with the oxygen sensing element in order to secure the reduction of the rise time. Conventionally, in order to the rise time reduction, the oxygen sensing element is uniformly heated and the heating member is disposed coaxially with the oxygen sensing element. Therefore, the contact portion of the heating member with the oxygen sensing element has been set between the extreme end of the heating member and the inner surface of the extreme end of the oxygen sensing element.

SUMMARY OF THE INVENTION

It is an object of the present invention to provide an oxygen sensor with a heater which can well sense an oxygen concentration in the exhaust gases from the internal combustion engine even under a condition that the exhaust gas temperature is low, for example, at the engine start or the time of idling, by quickly and efficiently heating an oxygen sensing element of a hollowed shaft-like member by a heating member contained in the sensing element, and can suppress a variation of the characteristics of the sensors to the minimum.

An oxygen sensor according to the present invention has a shaft-like heating member disposed within an oxygen sensing element of a hollowed shaft-like member with the closed end, in which the center line of the heating member is eccentric to the center line of the hollow of the oxygen sensing element in the vicinity of the heating portion of the heating member.

BRIEF DESCRIPTION OF THE DRAWINGS

In the accompanying drawings:

FIGS. 9A to 9C are views showing a terminal member of FIG. 8;

FIGS. 10A and 10B are views showing an assembly in which the terminal member is assembled into a heating member;

DETAILED DESCRIPTION OF THE INVENTION

Figure 1:
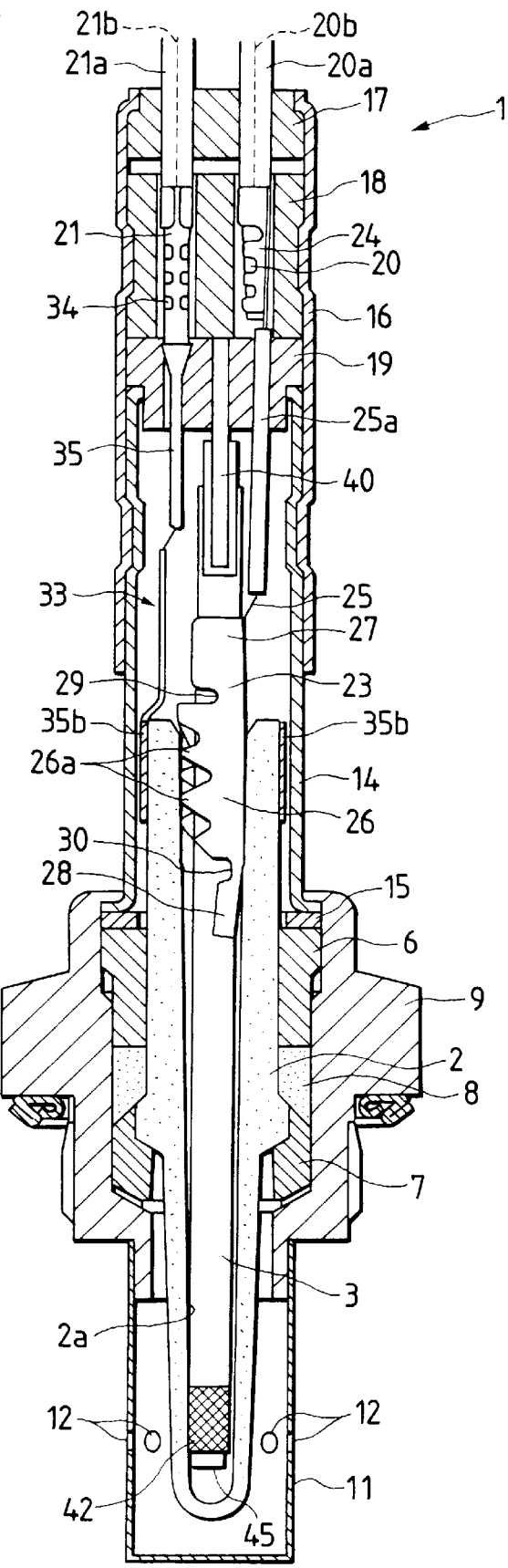
FIG. 1 is a longitudinal sectional view showing an oxygen sensor according to an embodiment 1 of the present invention.

The detailed description of the present invention will be described as follows.

In an oxygen sensor according to the present invention having a shaft-like heating member disposed within an oxygen sensing element of a hollowed shaft-like member with the closed end, the center line of the heating member is eccentric to the center line of the hollow of the oxygen sensing element in the vicinity of the heating portion of the heating member.

Incidentally, in the oxygen sensor according to the present invention, the heating element does not attach to the inner bottom end of the oxygen sensing element.

As the result of such a eccentricity, the surface of the heating portion of the heating member is preferably abutted on the inner wall of a hollowed space of the oxygen sensing element.

When the center line of the heating member is eccentric to the center line of the hollow of the oxygen sensing element, a portion of the oxygen sensing element closer to the heating member is more heated, and a heat distribution over the circumference of the oxygen sensing element may not be uniform. However, according to the structure of the present invention, an activation time of the oxygen sensor is possible to be shorter than of the conventional sensor.

In the side-abutting structure in which the heating member is sideways abutted on the inner wall of the oxygen sensing element, heat generated in the heating portion of the heating member is directly transferred from the heating element to the oxygen sensing element through the contact portion. Heat radiated from a portion around the contact portion additively heats the oxygen sensing element. Therefore, the oxygen sensing element is swiftly heated. That is, an activation time of the sensor is reduced. If the heating portion and the oxygen sensing element are thermally expanded, the structure in which the heating portion of the oxygen sensing element is sideways abutted on the inner wall of the oxygen sensing element is less affected by the thermal expansion than the structure in which the extreme end of the heating portion is abutted on the inner surface of the extreme end of the oxygen sensing element. In other words, if the heating portion and the oxygen sensing element have a heat history (frequently heated and cooled), the side-abutting structure can retain a good contact of them.

In the structure in which the heating portion of the oxygen sensing element is sideways abutted on the inner wall of the oxygen sensing element, the direct heat transfer owing to the contact and the radiation heat cooperate to provide a more efficient heat transfer than the end-to-end contact structure. The fact that a stable contact of the oxygen sensing element and the heating portion of the heating member is ensured leads to the lessening of the nonuniformity of a heat distribution over the oxygen sensing element, and hence the lessening of a variation of the characteristics of products of oxygen sensors.

The electrode layers may be respectively layered on the inner and outer surfaces of the oxygen sensing element. In this case, the electrode layers are electrodes (for example, Pt porous electrodes) having a catalytic function (oxygen dissociation catalytic function) to a dissociation reaction of oxygen molecules for injecting oxygen into the solid electrolyte of the oxygen sensing element and a recombination reaction of oxygen to cause the solid electrolyte to emit oxygen. The reason why, if the oxygen sensing element is locally heated, a rise time of the sensor is retained at a value substantially equal to that of the rise time of the conventional sensor, or more reduced than of the conventional one, may be estimated as below.

The oxygen sensor of this type operates in the following. A reference gas, such as air, is introduced into the inside of the oxygen sensing element, and a gas to be measured, such as an exhaust gas, is applied onto the outside of the oxygen sensing element.

An oxygen concentration in a gas under measurement is detected in terms of an electromotive force, which is generated in the oxygen sensing element depending on a difference between the oxygen concentrations inside and outside the oxygen sensing element. In order to cause the oxygen sensing element constructed with oxygen ion conductive solid electrolyte to produce a sufficient electromotive force, it is necessary that an electric resistance of the oxygen sensing element is sufficiently small, and that the catalytic activity of the electrode layers to the dissociation and the recombination reaction of oxygen molecules is sufficiently high. An output level of the oxygen sensor is determined depending on a compromise between an electric resistance value of the oxygen sensing element and the catalytic activity of the electrode layers.

A catalytic activity of the porous electrode made of Pt, for example, tends to more greatly increase with respect to temperature in comparison with an oxygen ion mobility of solid electrolyte of a $ZrO_2$ group, for example. When the oxygen sensing element is locally heated through the structure of the present invention, the electric resistance of the oxygen sensing element less decreases due to a solid electrolyte activation than in the conventional structure in which the oxygen sensing element is disposed coaxial with the heating member for coping with the problem of nonuniform heating. In this case, a heated portion of the oxygen sensing element is higher in temperature than in the conventional structure, so that the catalytic activity is increased at the portions of the electrode layers corresponding in position to the heated portion. With the increase of the catalytic activity of the electrode layer, the dissociation of the oxygen molecules in the gas under measurement is promoted, so that the electromotive force of the solid electrolyte and hence the output level of the sensor are increased, and the activation time (rise time) of the sensor is equal to the conventional one or reduced to be shorter than the conventional one.

In the present invention, the following structure may be used: The heating member is eccentric to the oxygen sensing element, but the surface of the heating portion of the heating member is put in proximity to the inner wall of the oxygen sensing element, viz., not in contact with the latter. In the structure more heat is radiated from the heating portion to the oxygen sensing element than in the structure having no eccentricity of the heating member from the oxygen sensing element. This also contributes to the reduction of the activation time of the oxygen sensor.

In the oxygen sensor of the invention, it is preferable that a difference ΔD between the inside diameter DA of the sensing element and the outside diameter DB of the heating member is shorter than 0.35 mm. The diameter of the inside of a cross section of the oxygen sensing element and the diameter of the outside of a cross section of the heating member, respectively, means the inside diameter of the oxygen sensing element and the outside diameter of the heating member when the inner surface of the oxygen sensing element and the outer surface of the heating member are cylindrical surfaces. When the inner surface of the oxygen sensing element and the outer surface of the heating member are not circular in cross section, those are converted into the surfaces circular in cross section by calculations, and the inside diameter and the outside diameters of those converted ones are used. When the diameter of the cross section varies (for example, the outer surface of the element and the member are tapered in the lengthwise direction), an average value of the diameters of each of them, lengthwise measured, is used.

If ΔD=DA−DB exceeds 0.35 mm, the activation time of the oxygen sensing element and hence the sensor rise time are increased or the rise times of the products of oxygen sensors tend to be not uniform. The reason for this may be estimated such that, when the heating member is sideways abutted on the inner wall of the oxygen sensing element, if the difference Δ is large, forces to abut the heating member on the inner wall of the products tend to be not uniform. The difference ΔD is more preferably 0.30 mm or shorter. If the difference ΔD is shorter than 0.1 mm, it is difficult to insert the heating member into the oxygen sensing element, entailing the reduction of an efficiency of assembling the heating member to the oxygen sensing element. For this reason, the difference ΔD is preferably 0.1 mm or larger, more preferably 0.15 mm or larger. This range is applied to a case when the heating element is not abutted to the inner wall of the oxygen sensing element.

A ratio of the differences ΔD (ΔD=DA−DB) to the outside diameter DB of the heating member is preferably 0.13 or shorter. When the ratio ΔD/DB exceeds 0.13, the rise time of the sensor is longer or the characteristics of the products of oxygen sensors tend to be not uniform. Therefore, the ratio ΔD/DB is preferably set at 0.10 or smaller.

Further, in the present invention, a part of the heating portion of the heating member when viewed in the circumferential direction is low in a heat distribution over the heating portion, when the heating portion of the heating member may have a part on the circumferential direction which is low in a heat distribution, and the heating portion of the heating member is abutted on the inner wall of the oxygen sensing element at a position on the remaining portion. A heat generating resistor pattern is printed on a ceramic green sheet, the resultant is wrapped round the core member, and sintered, to thereby form a heating portion. In this case, the heat generating resistor pattern is thin on a portion where the ends of the ceramic green sheet with the resistor pattern printed thereon are located. The opposite side of the heating portion surface to the resistor pattern thin portion is preferably abutted against the inner wall of the oxygen sensing element. The resistor pattern thin portion may be brought into contact with the inner wall of the oxygen sensing element. Also in this case, a given heat transfer can be secured. When the portion sufficiently generating heat, rather than the resistor pattern thin portion, is brought into contact with the inner wall of the oxygen sensing element, a more effective heat transfer is secured. Since the heating portion of the heating member locally exists when viewed in the circumferential direction, thermal energy is concentrated in a smaller volume. This unique feature is effective particularly for the reduction of the activation time after the current is fed to the heater.

The heating portion may be located closer to one end of the heating member. This unique feature is effective for swiftly heating the oxygen sensing element. The heating portion may be formed over the entire surface of the heating member. In this case, thermal energy tends to disperse. To secure an effective heating of the oxygen sensing element, it is desirable to locate the heating portion closer to one end of the heating member since heat is generated locally or at a local part. The locally generated heat and the side-abutting structure cooperate to more reduce the activation time of the sensor.

In the present invention, the heating member may be assembled into the oxygen sensing element by means of a terminal member, and the heating portion of the heating member is pressed against the inner wall of the oxygen sensing element by the terminal member. This feature makes the side-abutting structure stable and further suppresses the characteristic variation of the sensor products.

Preferably, the terminal member includes a heating member holder for holding the heating member, at least one internal electrode connector circumferentially surrounding the heating member and in contact with the electrode layer layered on inner wall of the oxygen sensing element, and a guide for pushing the heating member in the direction orthogonal to the axial direction of the heating member, the guide being provided at the opposite end to the end having the heating member holder. In the construction, the center line of the heating member is eccentric to the center line of the hollowed space of the oxygen sensing element by the guide, whereby the surface of the heating portion of the heating member is pressed against and fixed to the inner wall (referred frequently to as element inner wall) of the hollowed space of the oxygen sensing element. This feature in which the guide presses the heating member against the element inner wall makes it easy to realize the side-abutting structure.

From the viewpoint of reaction forces generated in the heating member, an elastic force of the guide is reduced to such an extent that the guide is able to withstand a bending moment resulting from a combination of a reaction force acting on the heating member in the inner wall of the oxygen sensing element acting on the heating member, a reaction force acting on the heating member in the guide, and a reaction force acting on the heating member in the heating member holder. In other words, the elastic force of the guide is used for pressing the heating member against the element inner wall. By properly adjusting the elastic force, a pressing state as an active form of contact can stably be sustained while protecting the heating member from its damage.

As a specific form to reduce the elastic force of the guide, the terminal member includes a constricted coupling part for coupling the guide and the internal electrode connector and/or a constricted coupling part for coupling the internal electrode connector and the heating member holder. With the provision of the coupling part, the elastic force of the guide is properly reduced to effectively avoid the damage of the heating member. When the heating member is deformed by a thermal stress generated therein, the coupling part is elastically deformed (or plastically deformed), to thereby lessen the deformation of the heating member by the thermal stress. This useful effect can also be expected when the coupling part is used.

As another preferred form of the terminal member, the terminal member includes an internal electrode connector circumferentially surrounding the heating member and in contact with the electrode layer layered on inner wall of the oxygen sensing element, a first heating member holder for holding the heating member, the first heating member holder being formed integral with the internal electrode connector while being located at one end of the internal electrode connector when viewed in the axial direction of the heating member and surrounding the heating member, and a second heating member holder for holding the heating member, the second heating member holder being formed integral with the internal electrode connector while being located at the other end of the internal electrode connector when viewed in the axial direction of the heating member and surrounding the heating member, and the axial center line of the second heating member holder being eccentric to the axial center line of the first heating member holder, wherein the axial center line of the heating member is slanted to the axial center line of a hollowed space of the oxygen sensing element by the first and second heating member holders of which the axial center lines are eccentric to each other, whereby the heating portion of the heating member is pressed against the inner wall of the hollowed space. In thus constructed terminal member, the axial center line of the heating member is slanted to the axial center line of a hollowed space of the oxygen sensing element by the first and second heating member holders of which the axial center lines are eccentric to each other, whereby the heating portion of the heating member is pressed against the inner wall of the hollowed space, and fastened thereto. The heating member is pressed against the element inner wall while being slanted by the first and second heating member holders of which the axial center lines are eccentric. Therefore, the side-abutting structure may easily be realized with the aid of the thus constructed terminal member. Therefore, the heating member can stably hold its slanted state, so that the side-abutting effect of the heating member is further enhanced.

More specifically, the first heating member holder and the second heating member holder may be coupled with respective corresponding end portions of the internal electrode connector in the same side of the periphery of the heating element in the diameter direction, and the axial center line of the first heating member holder may be farther than the axial center line of the second heating member holder with respect to the coupling parts thereof. When the heating portion is formed in the distal end of the heating member, the heating portion of the heating member is slanted to the coupling parts and abutted on the element inner wall on the coupling parts side. Where the output terminal (or ground terminal) of the oxygen sensing element is provided while being protruded from the end of the first heating member holder, which is opposite to the end thereof having the internal electrode connector, at a position corresponding to the coupling parts. When the heating member is disposed as mentioned above, in assembling the oxygen sensor, the heater terminals (formed at the end of the heating member opposite to the end thereof having the heating portion) of the heating member is made to little interfere with the lead-out terminal. Then, the assembling work of the oxygen sensor is easy.

Moreover, the axial center lines of the first heating member holder and the internal electrode connector may be substantially coincident with each other, and the axial center line of the second heating member holder may be eccentric to the coupling parts from the axial center line of the internal electrode connector. When first heating member holder is coaxial with the internal electrode connector, a space between and along the oxygen sensor and the combination of the connector and the lead-out wire is relatively uniform. Therefore, an insulation trouble between them, for example, will hardly take place.

The terminal member may include a constricted coupling part for coupling the first heating member holder with the internal electrode connector and/or another constricted coupling part for coupling the second heating member holder with the internal electrode connector. When the heating member is held by the two holders, these holders are likely to hold down the thermal expansion and contraction of the heating member. However, the coupling part is elastically deformed or plastically deformed, to thereby lessen the deformation of the heating member by the thermal stress, and hence making it difficult to damage the heating member.

The constricted coupling part (referred to as a first coupling part) for coupling the first heating member holder with the internal electrode connector and the constricted coupling part (referred to as a second coupling part) for coupling the second heating member holder with the internal electrode connector may be stepwise and inward bent in the radial direction of the internal electrode connector. In the construction, by adjusting a degree of the bending, a proper eccentricity between the axial center lines of the first and second heating member holders is secured.

Preferred embodiments of the present invention will be described with reference to the accompanying drawings.

Embodiment 1

An oxygen sensor 1 is assembled from an oxygen sensing element 2 as a solid electrolyte, hollowed shaft-like member with the closed end, a shaft-like heating member 3 as a ceramic heater, and various parts forming an outer shell covering them. The oxygen sensing element 2 is made of solid electrolyte of an oxygen iron conduction. A typical example of the solid electrolyte is $ZrO_2$ as a solid solution of $Y_2O_3$ or CaO, or a solid solution of $ZrO_2$ and an oxide of an alkaline-earth metal or a rare-earth metal. $HfO_2$ may be contained in $ZrO_2$ as a base. Such a type of the oxygen sensor according to the present invention is preferably used as an air fuel ratio sensor of a vehicle. $Y_2O_3$, CaO and/or $HfO_2$ are used as a partial stabilizing agent. Such a kind of sensor is called "partial stabilized zirconia type sensor".

Figure 2:
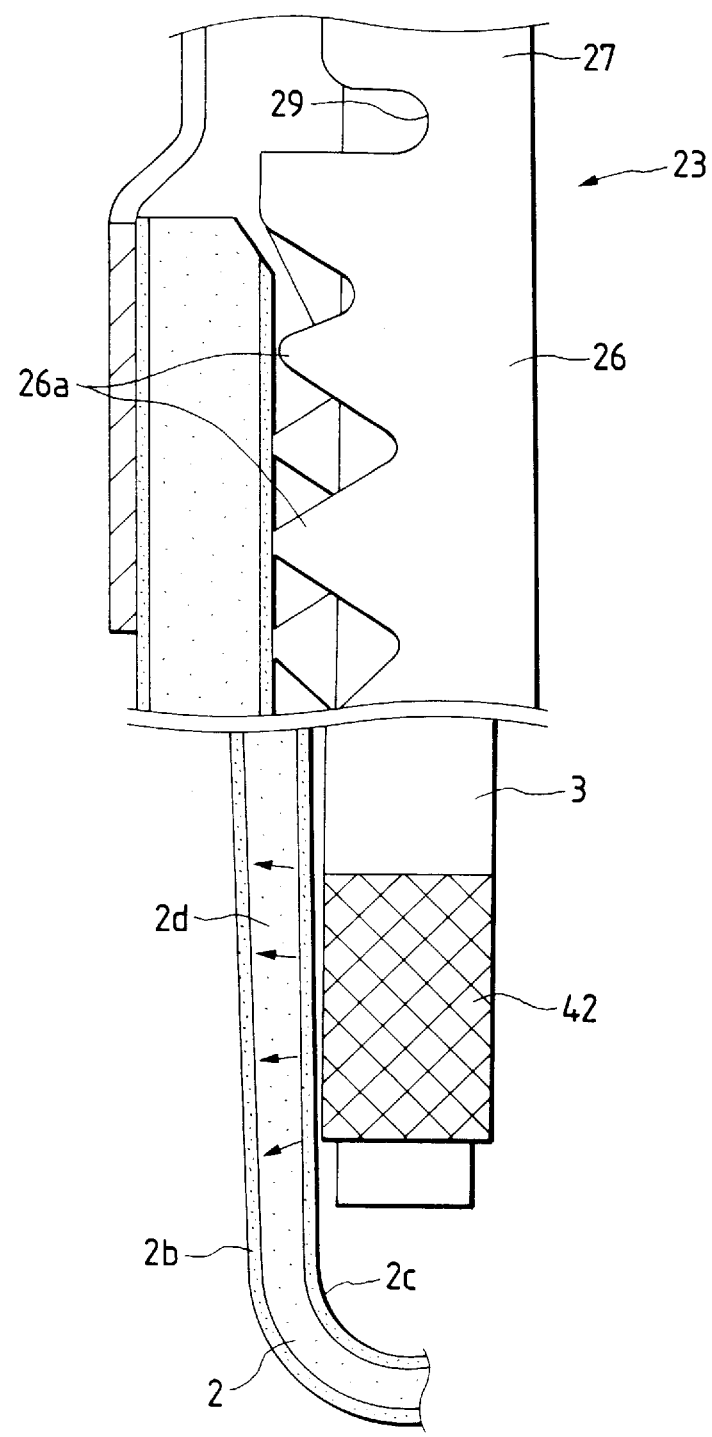
FIG. 2 is an enlarged, cross sectional view showing the contact position of a heating portion and an oxygen sensor element in the embodiment of FIG. 1.

The oxygen sensing element 2 is disposed passing through a housing 9 as a metal tubular member while being electrically insulated from the housing. Specifically, the housing 9 is disposed around the middle of the oxygen sensing element 2 in a state that insulators 6 and 7 of insulating ceramics and ceramic powdery material 8 of talc are inserted therebetween. As shown in FIG. 2, electrode layers 2b and 2c are layered entirely over the inner and outer surfaces of the oxygen sensing element 2, respectively. The electrode layers 2b and 2c are electrodes, for example, Pt porous electrodes, having a catalytic function (oxygen dissociation catalytic function) to a dissociation reaction of oxygen molecules for injecting oxygen into the solid electrolyte of the oxygen sensing element 2 and a recombination reaction of oxygen to cause the solid electrolyte to emit oxygen. The electrode may include Pd (palladium), Rh (rhodium) or the like.

A protector 11 is placed at one of the open ends of the housing 9, while covering the extreme end of the oxygen sensing element 2 with a space intervening therebetween. A plural number of gas holes 1 through which exhaust gases pass are formed in the protector 11. Through the gas holes, the oxygen contained in the exhaust gases comes in contact with the surface of the tip of the oxygen sensing element 2. A first sleeve 14 is fit to and caulked at the other open end of the housing 9 in a state that a ring 15 is placed between it and the insulator 6. A second sleeve 16 is fit and fixed to the first sleeve 14. The upper opening of the second sleeve 16 is sealed with a plug 17. Further, plugs 18 and 19 are located under the plug 17 within the second sleeve. Lead wires 20 and 21 are provided passing through the plugs 17 and 18.

The lead wire 20 is electrically connected to the inner electrode layer, not shown, of the oxygen sensing element 2, through a connector 24 of a terminal member 23, a lead-out wire 25 (covered with an insulating tube 25a) connected thereto, and an internal electrode connector 26 of the terminal member 23. The lead wire 21 is electrically connected to the outer electrode layer, not shown, of the oxygen sensing element 2, through a connector 34 of another terminal member 33, a lead-out wire 35 connected thereto, and an external electrode connector 35b. A pair of positive and negative heater terminals 40 for feeding current to the heating member 3 are fixed to the base (upper end in FIG. 1) of the heating member 3, and current is fed to a heating resistor circuit (to be described later), by way of the heater terminals 40. A pair of lead wires for the heater are connected to the pair of heater terminals 40, through the plugs 17 and 18.

In the thus constructed oxygen sensor 1, air as base gas is introduced into a space within the oxygen sensing element 2 through gaps formed between the cable wires 20b and 21b of covering layers 20a ad 21a of the lead wires 20 and 21. Exhaust gas is introduced through the gas holes 12 of the protector 11 and comes in contact with the outer surface of the oxygen sensing element 2. As a result, a battery electromotive force is generated in the oxygen sensing element 2. The generated electromotive force depends on an oxygen concentration difference between the inner and outer sides of the oxygen sensing element 2. The electromotive force is lead out through the lead wires 20 and 21 from the electrode layers 2b and 2c, in the form of a detecting signal representative of an oxygen concentration contained in the exhaust gas. When the exhaust gas temperature is sufficiently high, the oxygen sensing element 2 is heated by the exhaust gas, so that it is activated. When the exhaust gas is at low temperature at the engine start, for example, the oxygen sensing element 2 is forcibly heated by the heating member 3 to be activated.

Usually, the heating member 3 is a ceramic heater. In the ceramic heater, a ceramic bar 45 made mainly of alumina is used as a core member. A heating portion 42 is formed on the surface of the ceramic bar 45. The heating portion 42 consists of a resistor wire part (resistor pattern) 41 patterned in a zig-zag fashion. A predetermined pattern of resistor paste is printed on an outer ceramic portion 43 like a sheet. The outer ceramic portion 43 is wrapped round the ceramic bar 45, and sintered. The ceramic bar 45 is slightly projected outside from the extreme end of the outer ceramic portion 43. Current is fed to the resistor line part (resistor pattern) 41 through a current passage, not shown, extended from the heater terminals 40. The heating portion 42 is located at a portion of the heating member 3 closer to the extreme end thereof. Accordingly, heat is generated locally or in the extreme end portion of the heating member.

Figure 3:
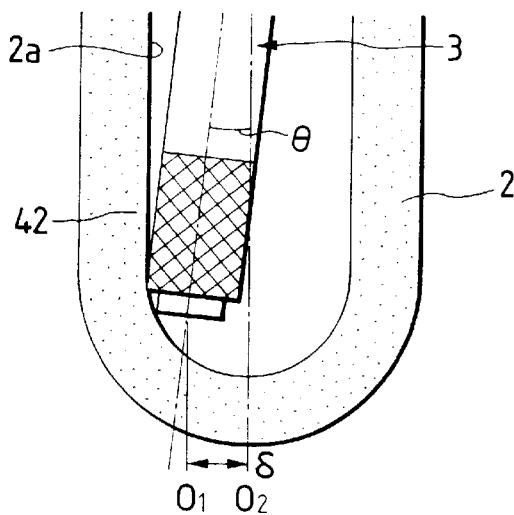
FIG. 3 is a partial cross sectional view conceptually showing a key portion of the embodiment.

As shown in FIG. 3, in the vicinity of the heating portion 42 of the heating member 3, the center line O1 of the heating member 3 is eccentric to the center line O2 of the oxygen sensing element 2 by a fixed distance δ. The surface of the extreme end of the heating portion 42 of the heating member 3 is in contact with the inner wall (referred also to as an element inner wall) 2a of a hollowed space of the oxygen sensing element 2, while being pressed against the element inner wall at predetermined surface pressure. As seen from FIG. 1, the contact position of the heating portion is preferably a position somewhat closer to the middle of the oxygen sensing element 2 than the closed end of the sensing element, preferably on the level of the gas holes 12 of the protector 11.

The inner wall of the oxygen sensing element 2 is tapered. A difference ΔD between an average value (referred merely to an inside diameter) DA of the inside diameter of the sensing element and the outside diameter DB of the heating member 3 is preferably 0.1 to 0.35 mm (ΔD=DA−DB), and more preferably 0.15 to 0.30 mm. A ratio of the difference ΔD to the outside diameter DB of the heating member 3 is 0.13 or shorter, preferably 0.10 or shorter. Further, the ratio of the difference ΔD to the outside diameter DB of the heating member 3 is preferably 0.06 or longer.

Figure 4:
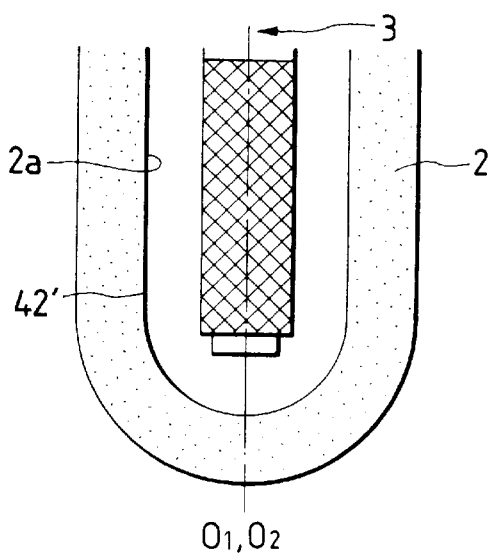
FIG. 4 is a partial cross sectional view conceptually showing a key portion of a conventional oxygen sensor.

FIG. 4 shows a structure of a conventional oxygen sensor, which corresponds to the already illustrated structure of the oxygen sensor of the invention. As shown in the conventional structure, the center line O1 of the heating member 3 is coaxial with the center line O2 of the oxygen sensing element 2. As seen from the comparison of the structure of FIG. 3, in the structure of the invention, the center line O1 of the heating member 3 is inclined at an angle θ to the center line O2 of the oxygen sensing element 2 in a state that the surface of the extreme end of the heating portion 42 of the heating member 3 is pressed against the inner wall 2a of the hollowed space of the oxygen sensing element 2. The structure of the invention may be called a side-abutting structure. In FIGS. 3 and 4, for ease of understanding, the gap between the heating member 3 and the oxygen sensing element 2 and the inclination of θ of the former to the latter are illustrated in an exaggerating manner. Actually, the fixed distance δ and the inclination θ are approximately 0.085 to 0.385 mm and 0.1° to 0.5° when the inside diameter defined by the element inner wall 2a is 2.8 to 3.2 mm and the outside diameter of the heating member 3 is 2.7 to 3 mm. By so selecting, a reliable side-abutting structure is secured without giving rise to an excessive pressure between the heating member 3 and the oxygen sensing element 2. Further, it is noted that the heating portion 42 of FIG. 3 occupies a narrower region deviated to one side in the distal end portion of the heating member 3 than the heating portion 42' of FIG. 4.

Figure 5A:
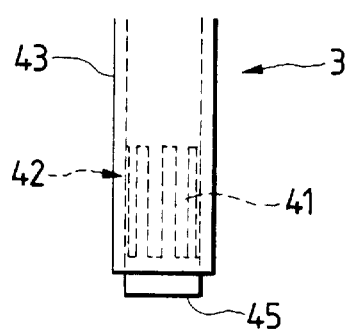
FIGS. 5A and 5B are views showing an example of the heating portion of FIG. 1.
Figure 5B:
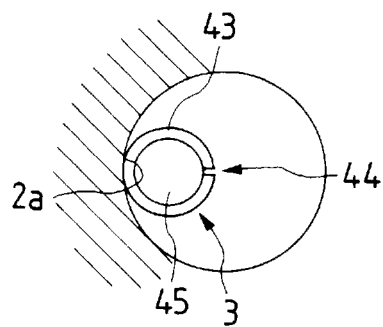

As shown in FIGS. 5A and 5B, when the outer ceramic portion 43 of the heating member 3 is wrapped round the ceramic bar 45, a slit 44 is formed between the ends of the outer ceramic portion 43 wrapped round the outer surface of the heating member 3, while being axially extended. The resistor pattern 41 is absent along the slit 44 and its near portions, and less heat is generated along these portions. Therefore, when the surface of the heating portion 42 is abutted against the element inner wall 2a of the heating member 3, the opposite side of the heating portion surface to the slit 44 side is preferably abutted against the element inner wall of the heating member. By so doing, heat is directly and efficiently transferred from the heating generating portion to the oxygen sensing element 2.

The terminal member 23 functions to elastically press the heating portion 42 of the heating member 3 against the element inner wall 2a. In this case, the terminal member 23 has three functions. First, the terminal member 23 serves as an output terminal of the inner electrode layer of the oxygen sensing element 2 and electrically connects the oxygen sensing element 2 to the lead wire 20. Second, the terminal member 23 fixes the heating member 3 to the inside of the oxygen sensing element 2. This function is the same as of the conventional sensor. Third, the terminal member 23 elastically presses the extreme end of the heating member 3 against the element inner wall 2a to form the side-abutting structure. In this case, a guide 28 mainly gives rise to the elastic force. The guide 28 is formed at one end of the terminal member 23.

Figure 6A:
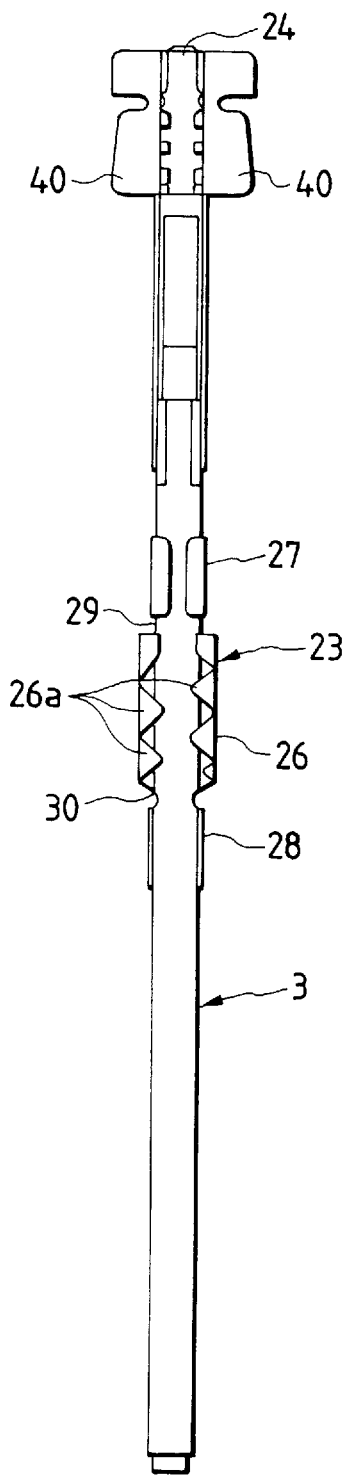
FIGS. 6A and 6B are views showing an assembly in which an terminal member is assembled into a heating member.
Figure 6B:
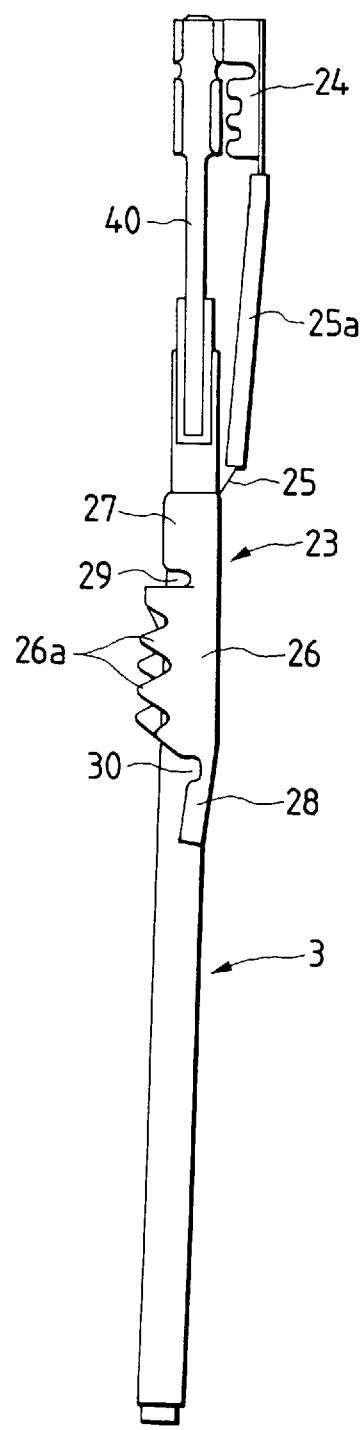
Figure 7A:
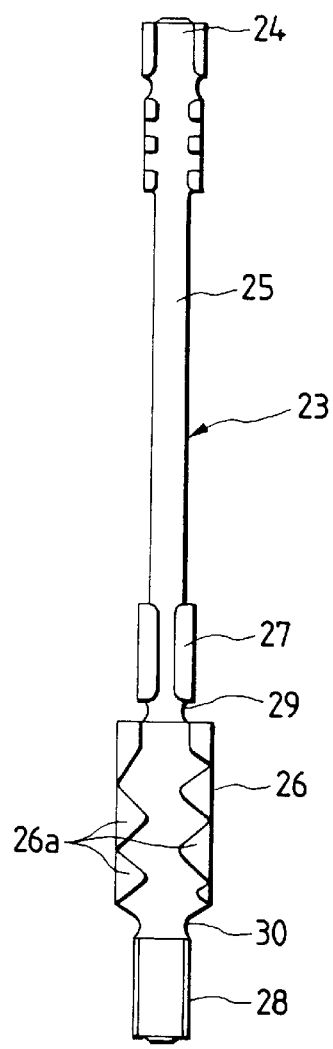
FIGS. 7A and 7B are views showing the terminal member of FIG. 6.
Figure 7B:
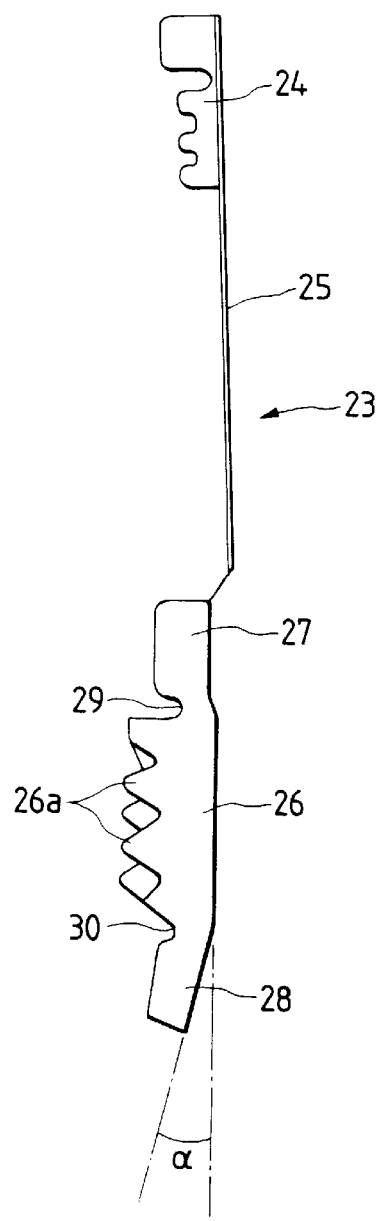

FIGS. 6A and 6B show the terminal member 23 being assembled into the heating member 3, and FIGS. 7A and 7B show the terminal member 23 alone. As seen from these figures, the internal electrode connector 26 of the terminal member 23 includes a heating member holder 27 at the base and the guide 28 at the distal end (i.e., opposite to the end having the heating member holder 27 formed thereat). The heating member holder 27 is put round the outer surface of the heating member 3 while being shaped in a letter C in cross section, and caulked thereon. The heating member holder 27 is provided at only one end of the internal electrode connector 26. The internal electrode connector 26 surrounds the outer surface of the heating member 3 except a part of the outer surface thereof, while being spaced from the heating member 3 by a predetermined gap therebetween. The internal electrode connector 26 comes in contact with the inner electrode layer of the oxygen sensing element 2.

In the present embodiment, to form the internal electrode connector 26, a plate-like or major portion of a blank sheet having saw-tooth contact parts 26a extended from both sides thereof are bent into a cylindrical member, which may surround the heating member 3. The saw-tooth contact parts 26a of the internal electrode connector 26 are staggered in shape such that the tops of the saw-tooth of one contact are aligned with the bottoms of the other contact. If so done, in the work of assembling, when the internal electrode connector 26 is inserted into the oxygen sensing element 2, it rarely happens that both the saw-tooth contact parts 26a are caught at the edge of the opening of the oxygen sensing element 2. This leads to an easy assembling of the internal electrode connector 26 to the oxygen sensing element 2. It is preferable that the saw-tooth contact parts 26a is shaped to be somewhat long. If so set, when the major portion of the blank sheet is bent into the internal electrode connector 26, the length of the blank sheet when viewed in the bending direction is increased, making easy to work.

The guide 28, which is the most essential part of the terminal member 23 under discussion, is semicircular in cross section and slanted at an angle α inward from the center line of the terminal member 23, more exactly the heating member holder 27 and the internal electrode connector 26, as shown in FIG. 7. The thus slanted guide 28 pushes the heating member 3 in the direction orthogonal to its axial direction to press it against the element inner wall 2a of the oxygen sensing element 2.

Between the heating member holder 27 and the internal electrode connector 26, the terminal member 23 is circumferentially cut out from both sides to form U-shaped cutouts or a constricted coupling part 29. The coupling part 29 couples the heating member holder 27 with the coupling part 29, and prevents a reaction force from being concentrated in the terminal member 23. Also between the internal electrode connector 26 and the guide 28, a constricted coupling part 30 is formed coupling them. The coupling part 30 properly adjusts its elastic force in the direction orthogonal to the axial direction, which acts on the heating member 3. The constricted coupling part 30 functions to reduce an elastic force of the guide 28. In the side-abutting structure of the heating member 3 shown in FIG. 1, an elastic pressure of the heating member 3 to the element inner wall 2a is applied mainly by the guide 28.

In this state, a reaction force of the element inner wall 2a acting on the heating member 3, a reaction force acting on the heating member 3 in the guide 28, and a reaction force acting on the heating member 3 in the heating member holder 27 are combined into a bending moment. A measure is taken to prevent the bending moment from breaking the heating member 3, in other words, to prevent generation of a reaction force outside a tolerable range of strength of the heating member 3. Means to adjust such a reaction force or such a bending moment are the guide 28, the constricted coupling part 30 adjacent thereto, another coupling part 30, and one heating member holder 27.

In manufacturing the thus constructed oxygen sensor 1, it is a common practice that after the terminal member 23 is fixed to the heating member 3, the resultant assembly is inserted into the oxygen sensing element 2. In the insertion process, the extreme end of the heating member 3 slides on the element inner wall 2a while elastically contacting with the element inner wall, so that the side-abutting structure is set up and the heating member 3 is fastened onto the oxygen sensing element 2, together with of the terminal member 23. Also in this process, the guide 28, the coupling part 30 and the like absorbs and lessens a reaction force generated in the heating member 3.

The side-abutting structure in which the heating member 3 is abutted on the element inner wall 2a, employed by the present embodiment, brings about many advantages. Heat generated in the heating portion 42 is swiftly transferred to the oxygen sensing element 2, and heats it. Heat radiated from a locally heated portion in the vicinity of the contact position of the heating portion 42 additively heats the oxygen sensing element 2. The heat conduction and the heat radiation cooperate to quickly heat the oxygen sensing element 2, to thereby reduce the time taken till the oxygen sensing element 2 is heated up to its activating temperature.

As shown in FIG. 2, the oxygen sensing element 2 is locally heated by the heating portion 42 that is disposed while being abutted on the element inner wall 2a of the oxygen sensing element 2. A rise time of the sensor is retained at a value substantially equal to that of the rise time of the conventional sensor shown in FIG. 4, or more reduced than of the conventional one. The reason for this, estimated by us, follows. In order to cause the oxygen sensing element 2 constructed with oxygen ion conductive solid electrolyte to produce a sufficient electromotive force, it is necessary that an electric resistance of the oxygen sensing element 2 is sufficiently small, and that the catalytic activity of the electrode layers 2b and 2c to the dissociation and the recombination reaction of oxygen molecules is sufficiently high. An output level of the oxygen sensor is determined depending on a compromise between an electric resistance value of the oxygen sensing element 2 and the catalytic activity of the electrode layers 2b and 2c.

When the oxygen sensing element 2 is locally heated by the heating portion 42 of the heating member 3, the electric resistance of the oxygen sensing element 2 less decreases due to a solid electrolyte activation than in the conventional structure. In this case, a heated portion 2d of the oxygen sensing element 2 is higher in temperature, so that the catalytic activity is increased at the portions of the electrode layers 2b and 2c corresponding in position to the heated portion. With the increase of the catalytic activity of the electrode layer 2b, the dissociation of the oxygen molecules in the gas under measurement is promoted, so that the electromotive force of the solid electrolyte and hence the output level of the sensor are increased, and the activation time (rise time) of the sensor is reduced to be shorter.

In our experiment, the following facts were confirmed. In the conventional sensor structure, when a heater resistance value was 3 to 3.5Ω, approximately 20 seconds were taken till the sensor activation temperature was reached. In the case of the side-abutting structure shown in FIG. 2, at the same resistance value, approximately 15 seconds were taken till the activation temperature was reached when the heating member was merely eccentric, and approximately 9 seconds were taken when the heating member was eccentric and abut on the inner wall of the hollowed oxygen sensing element. Thus, the rise time of the sensor is remarkably reduced. From these facts, it is seen that even when the exhaust gas temperature is low, e.g., at the start of the automobile engine or at the time of idling, the oxygen sensor properly senses an oxygen concentration at an early stage, to thereby achieve the exhaust gas purification with more precise and at higher resolution.

Embodiment 2

Figure 8:
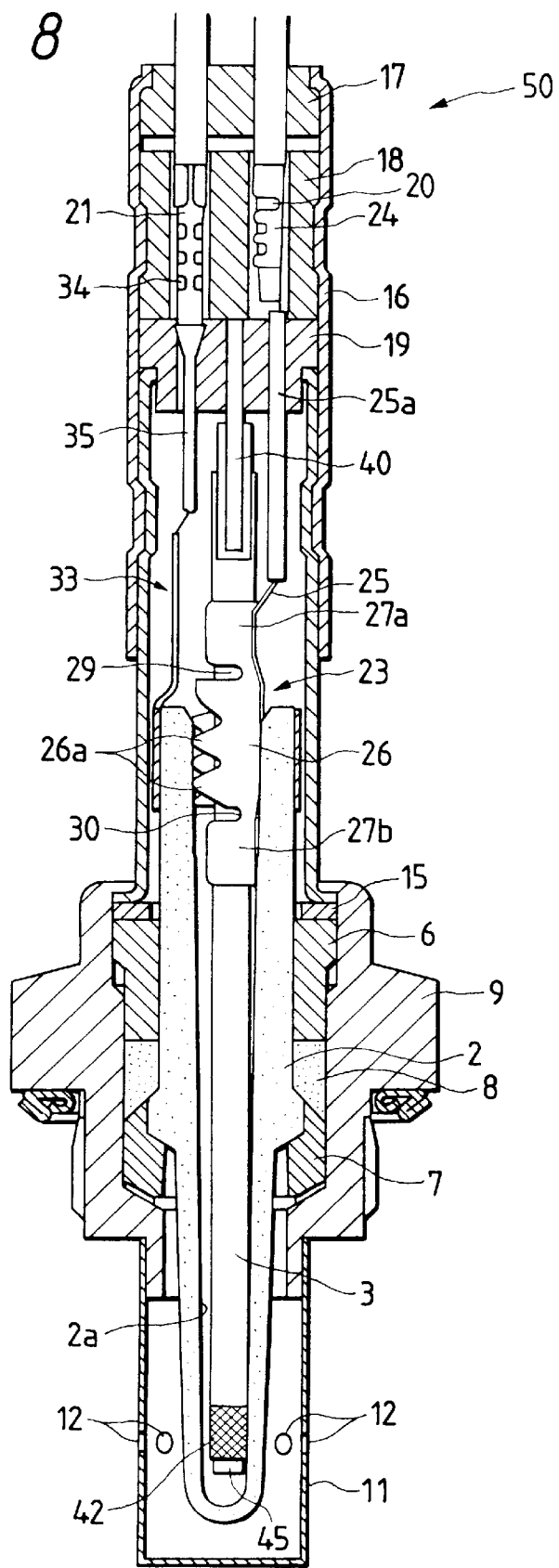
FIG. 8 is a longitudinal sectional view showing an oxygen sensor according to an embodiment 2 of the present invention.

FIG. 8 shows a second embodiment of an oxygen sensor according to the present invention. In the structure of an oxygen sensor 50 of the embodiment 2, the portions that are the same as or equivalent to those in the structure of the oxygen sensor 1 of the embodiment 1 are designated by like reference numerals, for simplicity. Description will be given placing emphasis on the differences of the sensor structure of the embodiment 2 from that of the embodiment 1.

The structure of the oxygen sensor 50 is different from that of the oxygen sensor 1 of the embodiment 1 in the following points. The terminal member 23 includes an internal electrode connector 26 substantially equal to that of the terminal member of the embodiment 1 (FIG. 1). The internal electrode connector 26 is provided with a first heating member holder 27a formed at one end when viewed in the axial direction of the heating member 3, and a second heating member holder 27b formed at the other end. Those first and second heating member holders are each substantially equal in construction to the heating member holder of the embodiment 1. As shown in FIGS. 9B and 9C, the axial center line O11 of the second heating member holder 27b is eccentric to the axial center line O10 of the first heating member holder 27a by a distance d. FIGS. 10A and 10B shows an assembly of the heating member 3 and the terminal member 23.

Figure 9A:
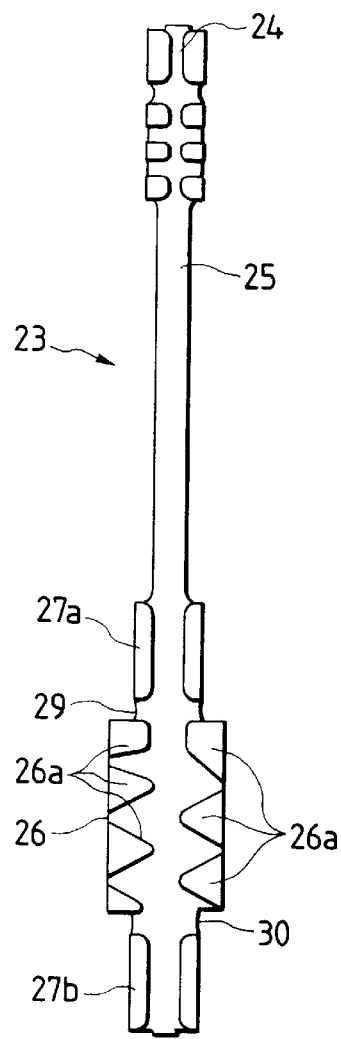
Figure 9A:
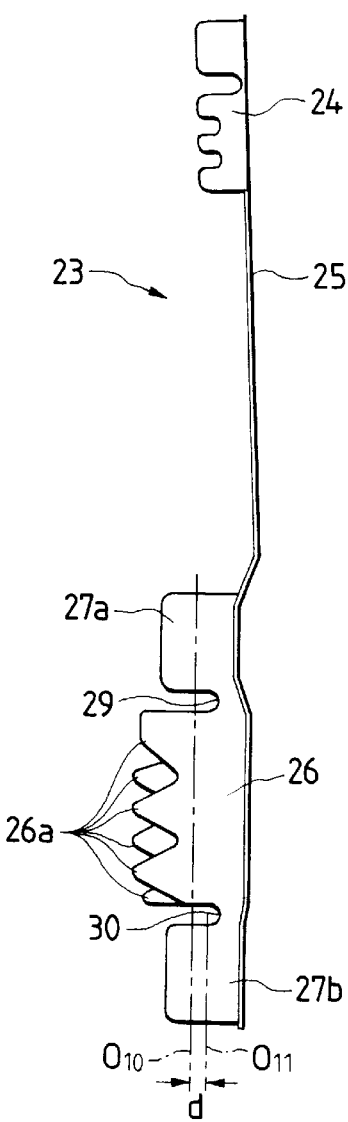
Figure 9C:
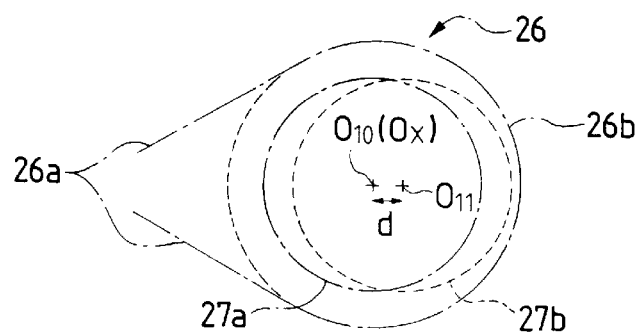

More specifically, as shown in FIGS. 9A and 9B, in the structure of the terminal member 23, the first heating member holder 27a and the second heating member holder 27b are integral with and extended from a part of the circumference of the heating member 3 while being disposed on both sides of the internal electrode connector 26 with a first coupling part 29 and a second coupling part 30 located therebetween as shown. The first coupling part 29 and the second coupling part 30 are stepwise bent inward in the radial direction of the internal electrode connector 26. A degree of the bending is adjusted so as to produce a proper distance or eccentricity d between the axial center lines O10 and O11 of the first and second heating member holders 27a and 27b.

In the present embodiment, the axial center line O10 of the first heating member holder 27a is farther than the axial center line O11 of the second heating member holder 27b from the first and second coupling parts 29 and 39 (connecting parts). More specifically, the center lines O10 and Ox of the first heating member holder 27a and the internal electrode connector 26 are substantially aligned with each other. The center line O11 of the second heating member holder 27b is eccentric to the coupling parts 29 and 30 from the center line Ox of the internal electrode connector 26. In the embodiment, as shown in FIG. 9C, a major portion 26b of the internal electrode connector 26 is wound round the cylindrical heating member 3, and the saw-tooth contact parts 26a are each contoured to be outward aslant to a tangential line at a point on a circumferential locus along the outer surface of the heating member 3, the saw-tooth contact part being extended from that point. The center line Ox of the internal electrode connector is the axial center line of the circumferential locus along which the major portion 26b is extended.

Figure 11A:
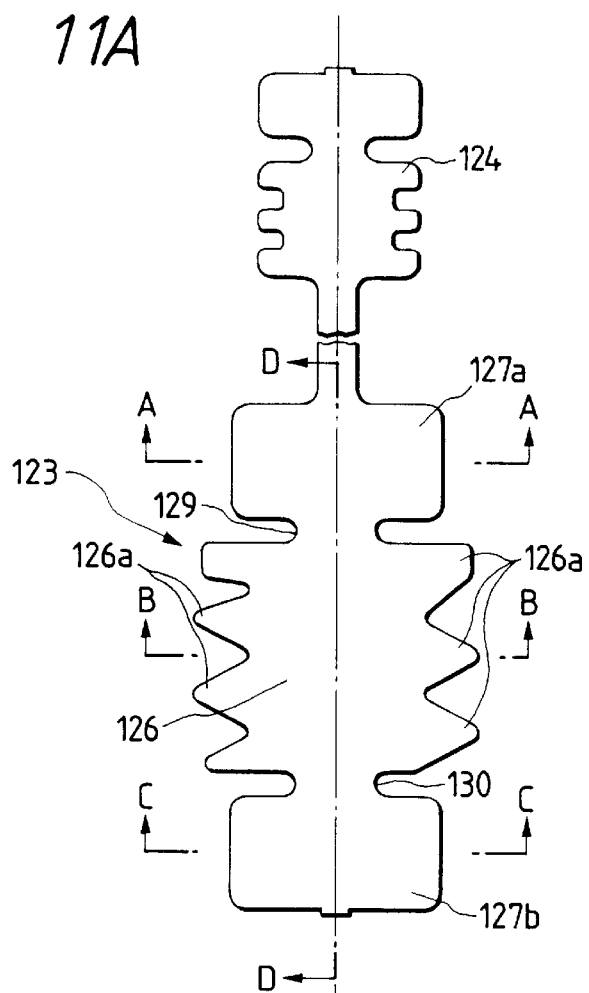
FIGS. 11A to 11E are views showing a blank sheet for forming the terminal member of FIG. 8.
Figure 11E:
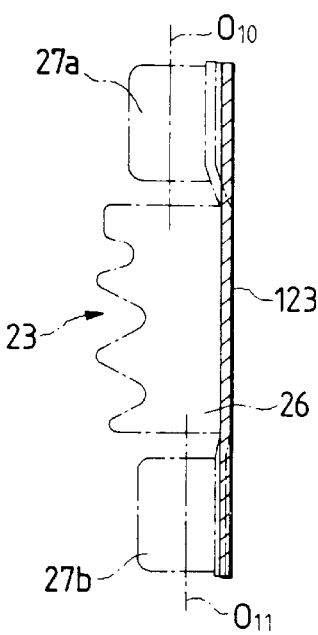
Figure 11B:
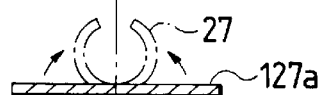
Figure 11C:
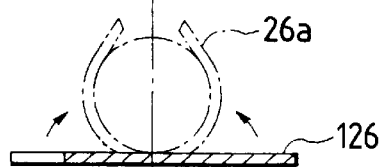
Figure 11D:
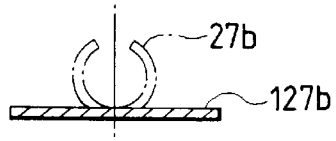

The terminal member 23 may be manufactured by properly bending a metal blank sheet 123 configured as shown in FIGS. 11A to 11D. As shown in FIG. 11A, the metal blank sheet 123 consists of three sections 127a, 126 and 127b. A connecting part 129 to be the first coupling part 29 connects the sections 127a and 126, and another connecting part 130 to be the second coupling part 30 connects the sections 126 and 127b. As shown in FIGS. 11B to 11D, the portions outwardly extended from both sides of the connecting parts 129 and 130 are curved so as to form a cylindrical member. The result is formation of the first heating member holder 27a, the internal electrode connector 26 and the second heating member holder 27b. The first coupling part 29 and the second coupling part 30, as shown in FIG. 11E, are stepwise bent so as to produce the eccentricity between the axial center lines O10 and O11 of the first and second heating member holder 27a and 27b.

In the thus constructed oxygen sensor 50, as shown in FIG. 8, the axial center line of the heating member 3 is slanted to the first coupling parts 29 and 30 of the terminal member 23 with respect to the axial center line of the hollowed space of the oxygen sensing element 2 (viz., it is slanted in the opposite direction in the embodiment 1 (FIG. 1)), by the first heating member holder 27a and the second heating member holder 27b. Thus, the heating portion 42 of the heating member 3 is pressed against the element inner wall 2a and fixed thereto. The heating member 3 is pressed against the element inner wall 2a while being slanted by the first and second heating member holders 27a and 27b of which the axial center lines are eccentric. Therefore, the heating member 3 can stably hold its slanted state, so that the side-abutting effect of the heating member 3 is further enhanced.

Figure 12:
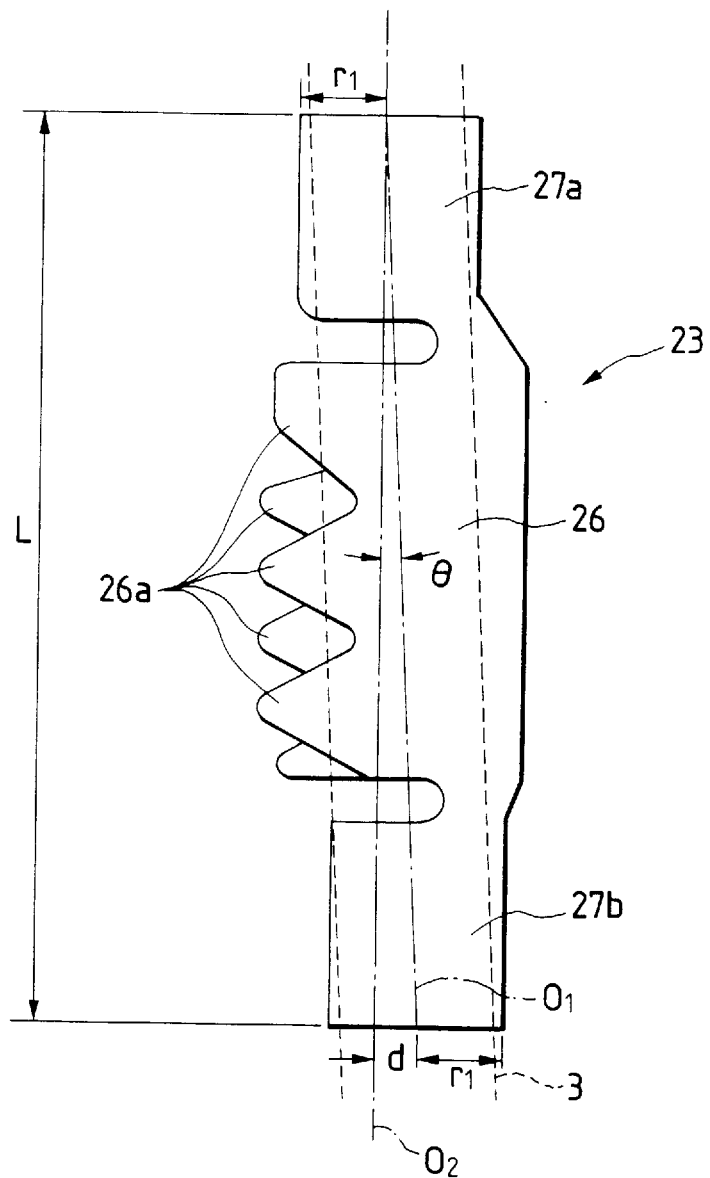
FIG. 12 is a view exaggeratedly showing an operation of the terminal member of FIG. 8.

The eccentricity d of the axial center line O10 of the first heating member holder 27a to that O11 of the second heating member holder 27b may be set as follows. As shown in FIG. 12 exaggeratedly illustrated for ease of understanding, an angle θ of the axial center line O1 of the heating member 3 to that O2 of the hollowed space of the oxygen sensing element 2 is preferably 0.1° to 0.5° as in the embodiment 1 when the inside diameter of the hollowed space defined by the element inner wall 2a is 2.8 to 3.2 mm and the outside diameter of the heating member 3 is 2.43 to 2.63 mm. When a distance between the end faces of the first and second heating member holders 27a and 27b (when viewed in the axial direction) is L, $\tan\theta = d/L$. $\tan 0.1°$ is approximately 0.0017, and $\tan 0.5°$ is approximately 0.0087. The eccentricity d is set to be within the following range: $0.0017 L \leq d \leq 0.0087 L$.

As stated above, the axial center line O10 of the first heating member holder 27a is farther than the axial center line O11 of the second heating member holder 27b with respect to the first and second coupling parts 29 and 30. This structural feature produces the following useful results. The heating portion 42 of the heating member 3 is slanted to the coupling parts 29 and 30 and abutted on the element inner wall on the coupling parts side. The connector 24 and the lead-out wire 25 (the output terminal of the oxygen sensing element 2) are provided while being protruded from the first heating member holder 27a at a position corresponding to the coupling parts 29 and 30. Since the heating member 3 is disposed while being slanted as mentioned above, in assembling the oxygen sensor 50, the heater terminals (power supply terminals) 40 of the heating member 3 is made to little interfere with the connector 24 and the lead-out wire 25. Then, the assembling work of the oxygen sensor 50 is easy. It is noted that the first heating member holder 27a is coaxial with the internal electrode connector 26. This feature creates a relatively uniform space between and along the oxygen sensor 50 and the combination of the connector 24 and the lead-out wire 25. Therefore, an insulation trouble between them, for example, will hardly take place.

While the preferred embodiments of the invention have been described, such description is for illustrative purposes only, and it should be understood that changes and variations may be made without departing from the spirit or scope of the invention.

EXAMPLE

The embodiments of the invention will be described in more detail by using an experimental example. Six combinations of the inside diameters (average values) DA each of the hollowed spaces defined by the tapered, element inner walls 2a of the oxygen sensing element 2 and the outside diameters DB of the heating members 3, as shown in Table 1, were used. 50 oxygen sensors 50 constructed as shown in FIG. 8 were manufactured for each combination. The oxygen sensing elements 2 were manufactured as sensing elements of $SrO_2$ solid electrolyte containing 8.5 to 9.0% by weight of $Y_2O_3$ in a manner that $ZrO_2$ powder combined with $Y_2O_3$ as a stabilizing agent is molded and the resultant is sintered. The values of the difference $\Delta D$ (=DA–DB) and the ratios $\Delta D/DB$ for those combinations are also shown in Table 1. The heating member 3 was inserted into the hollowed space to the depth of 47.4 mm. The depth was fixed at this value for those oxygen sensors. The size of the heating portion 42, measured in the axial direction of the heating member 3, was 4 mm, and an output power of it was 10 W when it is fed with electric power under 12V.

For the oxygen sensing elements 2 of those oxygen sensors 50, the lead wire 21 (the outer electrode layer 2b) is connected to the positive terminal of a constant DC voltage source (at 4V) through a resistor of 800 k$\Omega$, while the lead wire 20 (the inner electrode layer 2c) is earthed. In this state, current is fed, under 14V, to the heating portion 42 of the heating member 3, whereby the oxygen sensing element 2 is heated. A variation of an electrical resistance of each oxygen sensing element 2 was continuously monitored using a divided voltage applied to the oxygen sensing element 2. It was judged that the oxygen sensing element 2 had been activated at 5.6M$\Omega$ of the electric resistance. A time period ranging from an instance that the electric power feeding starts till the oxygen sensing element is activated was treated as a rise time of the sensor, and the rise time was measured every sensor. The average values and the standard deviations of the rise times of the sensors are shown in Table 1.

Variations of the average value Tav and the standard deviation $\delta T$ of sensor rise times with respect to the difference $\Delta D$ and $\Delta D/DB$ are plotted in FIGS. 13 and 14.

TABLE 1

| No. | DA (mm) | DB (mm) | $\Delta D$ = DA − DB (mm) | $\Delta D/$DB | Average Value Tav of Sensor Rise Time (sec) | Standard Deviation of Sensor Rise Time (sec) |
|---|---|---|---|---|---|---|
| 1 | 2.9 | 2.8 | 0.10 | 0.036 | 9.20 | 0.83 |
| 2 | 2.9 | 2.75 | 0.15 | 0.055 | 9.52 | 0.83 |
| 3 | 3.0 | 2.8 | 0.20 | 0.071 | 9.07 | 0.76 |
| 4 | 3.0 | 2.75 | 0.25 | 0.091 | 10.26 | 1.04 |
| 5 | 3.1 | 2.85 | 0.35 | 0.123 | 10.00 | 0.75 |
| 6 | 3.0 | 2.60 | 0.40 | 0.154 | 9.84 | 1.93 |

Figure 13A:
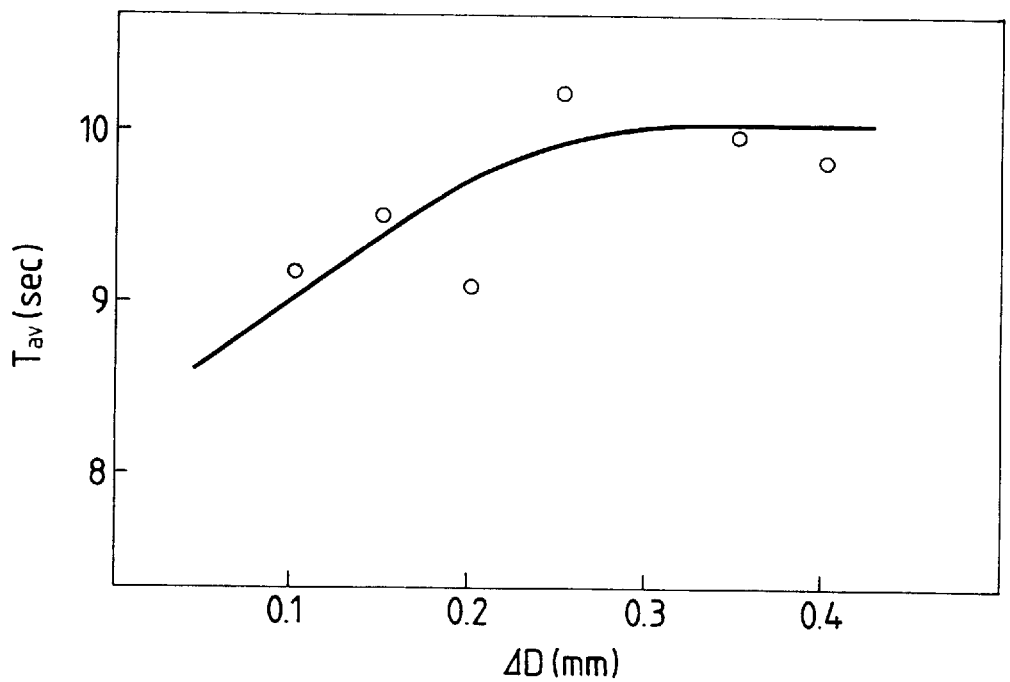
FIGS. 13A and 13B show graphs showing variations of the average value TAV and the standard deviation δT of sensor rise times obtained through experimental measurements with respect to the difference ΔD.
Figure 13B:
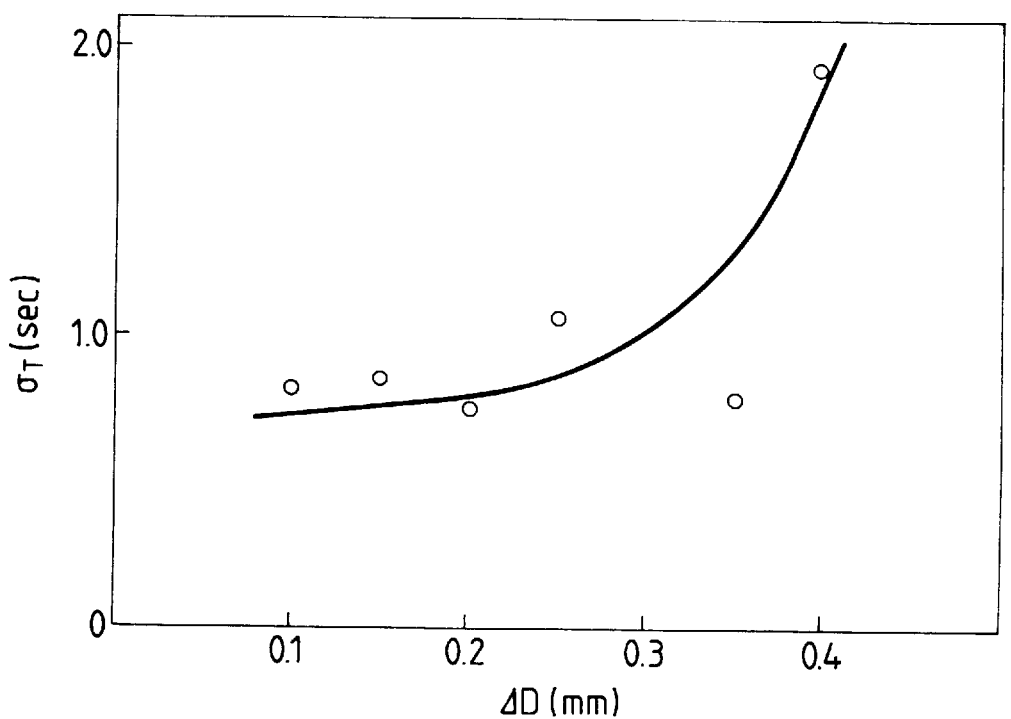
Figure 14A:
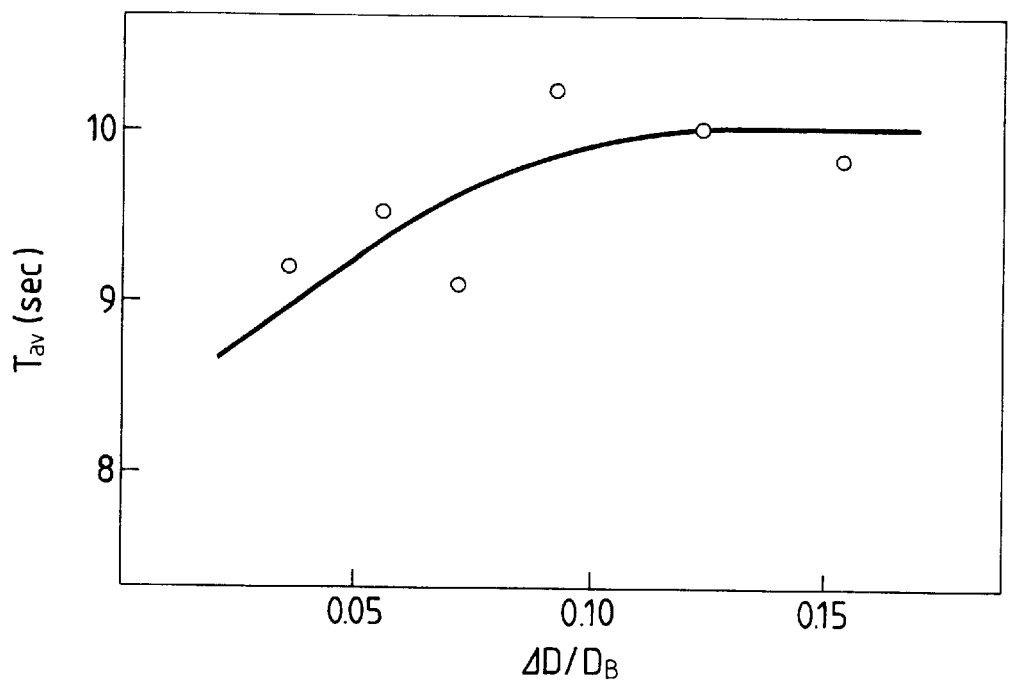
FIGS. 14A and 14B show graphs showing variations of the average value TAV and the standard deviation δT of sensor rise times obtained through experimental measurements with respect to ΔD/DB.
Figure 14B:
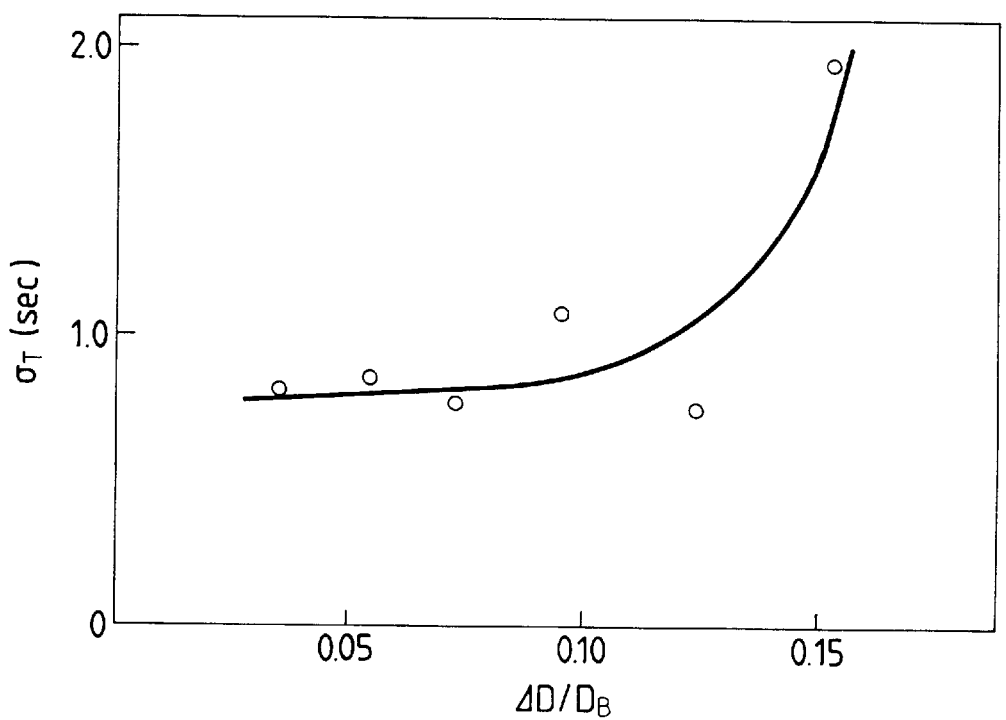

In FIGS. 13A and 13B, in the range of the difference $\Delta D$ up to about 0.25 mm, the average value of the rise time sharply increases with $\Delta D$. When $\Delta D$ exceeds 0.25 mm, a rate of an increase of $\Delta D$ becomes small. When $\Delta D$ exceeds 0.35, the standard deviation $\delta T$ of the rise time, or the scattering of rise time values of the individual sensors, abruptly increases. To suppress the scattering of rise time values of the individual sensors, $\Delta D$ is preferably set within 0.35 mm. Data plotted in FIGS. 14A and 14B teach that $\Delta D/DB$ is preferably set within 0.13 (more preferably 0.10 or smaller) to suppress the scattering of rise time values of the individual sensors.

According to the present invention, the sensor rising time is about 10 sec. However, the sensor rising time of one of conventional sensor in which the center line of the heating element is not eccentric to that of the hollow portion of the sensing element is about 40 to 60 sec. Further, even if the top end of the heating element is attached to the bottom of the sensing element, the sensor rising time is about 15 to 25 sec. Therefore, the rising time about 10 sec. accomplished by the present invention is very effective.

What is claimed is:

1. An oxygen sensor comprising:

an oxygen sensing element of a hollowed shaft-like member which is closed at one end and has electrode layers on the inner and outer sides thereof; and a shaft-like heating member, disposed within said oxygen sensing element, for heating said oxygen sensing element;

wherein a center line of said heating member is eccentric to a center line of a hollow portion of said oxygen sensing element in the vicinity of the heating portion of said heating member.

2. The oxygen sensor according to claim 1, wherein the center line of said heating member is eccentric to the center line of the hollow portion of said oxygen sensing element in the vicinity of a heating portion of said heating member, whereby the surface of said heating portion of said heating member is abutted on the inner wall of the hollowed space of said oxygen sensing element.

3. The oxygen sensor according to claim 1, wherein a difference $\Delta D$ between an inside diameter DA of said sensing element and an outside diameter DB of said heating member is equal to or shorter than 0.35 mm.

4. The oxygen sensor according to claim 1, wherein a ratio of a difference $\Delta D$ between an inside diameter DA of said sensing element and an outside diameter DB of said heating member to the outside diameter DB of said heating member is equal to or shorter than 0.13.

5. The oxygen sensor according to claim 1, wherein a part of said heating portion of said heating member in the circumferential direction is low in a heat distribution over said heating portion, and said heating portion of said heating member is abutted on the inner wall of said oxygen sensing element at a position on the remaining portion.

6. The oxygen sensor according to claim 1, wherein said heating portion is located closer to one end of said heating member.

7. The oxygen sensor according to claim 1, wherein said heating portion of said heating member is pressed against the inner wall of said oxygen sensing element.

8. The oxygen sensor according to claim 1, wherein said heating member is assembled into said oxygen sensing element by means of a terminal member, and said heating portion of said heating member is pressed against the inner wall of said oxygen sensing element by said terminal member.

9. The oxygen sensor according to claim 8, wherein said terminal member comprises:
   a heating member holder for holding said heating member;
   at least one internal electrode connector circumferentially surrounding said heating member and in contact with the electrode layer layered on inner wall of said oxygen sensing element; and
   a guide for pushing said heating member in the direction orthogonal to the axial direction of said heating member, said guide being provided at the opposite end to the end having said heating member holder;
   wherein the center line of said heating member is eccentric to the center line of the hollow portion of said oxygen sensing element by said guide, whereby the surface of said heating portion of said heating member is pressed against the inner wall of the hollowed space of said oxygen sensing element to be fixed.

10. The oxygen sensor according to claim 9, wherein an elastic force of said guide is reduced to such an extent that said guide is able to withstand a bending moment resulting from a combination of a reaction force acting on said heating member in the inner wall of said oxygen sensing element acting on said heating member, a reaction force acting on said heating member in said guide, and a reaction force acting on the heating member in said heating member holder.

11. The oxygen sensor according to claim 10, wherein said terminal member includes a constricted coupling part for coupling said guide and said internal electrode connector and/or a constricted coupling part for coupling said internal electrode connector and said heating member holder.

12. The oxygen sensor according to claim 8, wherein said terminal member comprises:
   at least one internal electrode connector circumferentially surrounding said heating member and in contact with the electrode layer layered on inner wall of said oxygen sensing element;
   a first heating member holder for holding said heating member, said first heating member holder being formed integral with said internal electrode connector while being located at one end of said internal electrode connector when viewed in the axial direction of said heating member and surrounding said heating member; and
   a second heating member holder for holding said heating member, said second heating member holder being formed integral with said internal electrode connector while being located at the other end of said internal electrode connector when viewed in the axial direction of said heating member and surrounding said heating member, and the axial center line of said second heating member holder being eccentric to the axial center line of said first heating member holder;
   wherein the axial center line of said heating member is slanted to the axial center line of a hollowed space of said oxygen sensing element by said first and second heating member holders of which the axial center lines are eccentric to each other, whereby said heating portion of said heating member is pressed against the inner wall of said hollowed space.

13. The oxygen sensor according to claim 12, wherein said first heating member holder and said second heating member holder are coupled with respective corresponding end portions of the internal electrode connector in the same side of the periphery of the heating element in the diameter direction, and the axial center line of said first heating member holder is farther than the axial center line of said second heating member holder with respect to the coupling parts of them.

14. The oxygen sensor according to claim 13, wherein the axial center lines of said first heating member holder and said internal electrode connector are substantially coincident with each other, and the axial center line of said second heating member holder is eccentric to the coupling parts from the axial center line of said internal electrode connector.

15. The oxygen sensor according to claim 14, wherein said terminal member includes at least one of a first coupling part for coupling said first heating member holder with said internal electrode connector and a second coupling part for coupling said second heating member holder with said internal electrode connector.

16. The oxygen sensor according to claim 15, wherein said first coupling part and said second coupling part are inward bent in the radial direction of said internal electrode connector to form a step portion, and a degree of the bending of said first and second coupling parts is adjusted so as to produce a proper eccentricity between the axial center lines of said first and second heating member holders.

17. The oxygen sensor according to claim 1, wherein the eccentric angle of the center line of said heating member with respect to the center line of a hollow portion of said oxygen sensing element is in the range of 0.1° to 0.5°.

18. The oxygen sensor according to claim 4, wherein the ratio of the difference ΔD (ΔD=DA−DB) to the outside diameter DB of said heating member is equal to or longer than 0.06.

19. The oxygen sensor according to claim 1, wherein said oxygen sensor is used as an air fuel ratio sensor of a vehicle.

20. The oxygen sensor according to claim 1, wherein said oxygen sensing element comprises zirconia.

21. The oxygen sensor according to claim 20, wherein said oxygen sensing element further comprises a partial stabilizing agent.

22. The oxygen sensor according to claim 21, wherein said partial stabilizing agent is at least one of $Y_2O_3$, CaO and $HfO_2$.

23. The oxygen sensor according to claim 1, wherein said electrode comprises platinum.

24. The oxygen sensor according to claim 23, wherein said electrode further comprises at least one of palladium and rhodium.

* * * * *